Dec. 21, 1954 F. SPANBAUER Plant Pat. 1,337
ROSE PLANT
Filed Jan. 5, 1954 2 Sheets-Sheet 1
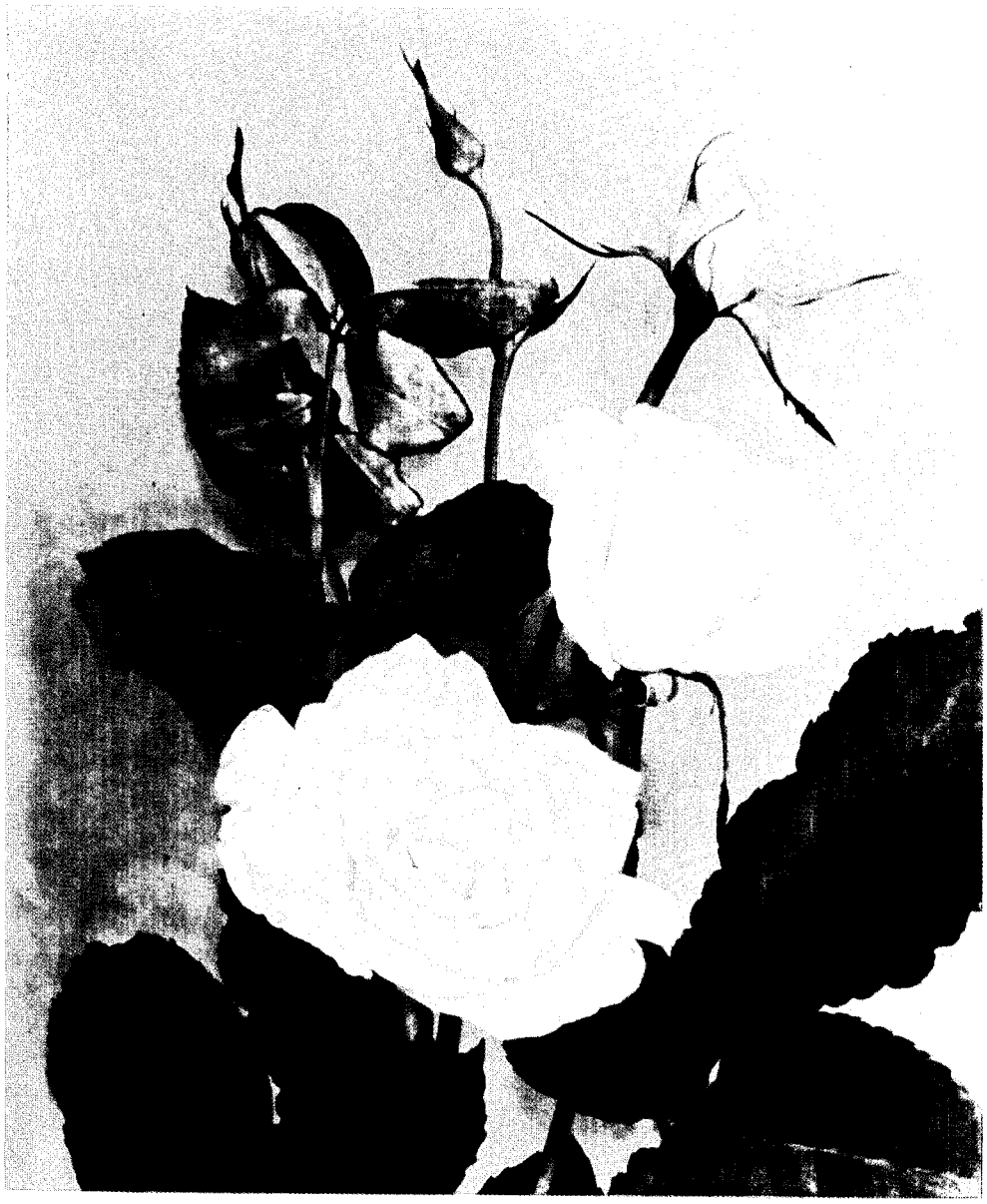
Inventor.
Frank Spanbauer
By: Robert Cobb
Attorneys.

Dec. 21, 1954 F. SPANBAUER Plant Pat. 1,337
ROSE PLANT
Filed Jan. 5, 1954 2 Sheets-Sheet 2
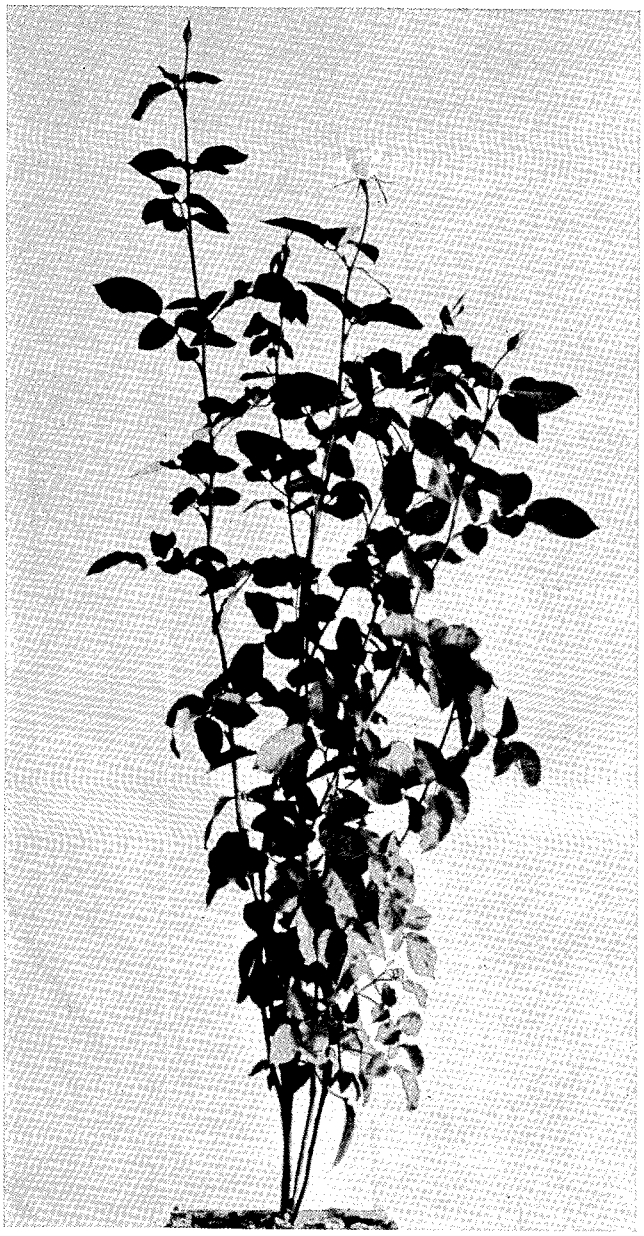
Inventor
Frank Spanbauer
By: Robb & Robb
Attorneys.

United States Patent Office

Plant Pat. 1,337
Patented Dec. 21, 1954

1,337

ROSE PLANT

Frank Spanbauer, Decatur, Ill.

Application January 5, 1954, Serial No. 402,422

1 Claim. (Cl. 47—61)

The present invention relates to a new and distinct variety of rose plant of the hybrid tea class, which was originated by me by crossing the variety "Ophelia" (unpatented) with the variety "Curlywhite" (unpatented).

As the result of this cross, I have produced a new variety of rose plant which is particularly characterized as to novelty by the substantially pure white color of its blooms which are comparable to the color of a white Easter lily when the rose is in full bloom; by its usually long pointed buds; by the relatively hard petals of its blooms and their resultant long-lasting quality which is superior to that of any previously known white rose; by its dark green, very thick and leathery foliage and its attendant good resistance to mildew and blackspot; by the relatively short neck of its blooms which results from the fact that the foliage grows to within 3 or 4 inches from the base of the flowers, thereby leaving no naked stems to detract from the decorative beauty of the plant and its flower; and by its habit of bearing blooms on heavy, thick and stiff stems which are capable of enduring the most adverse conditions.

The foregoing characteristics definitely distinguish my new variety from its parents, as well as from all other varieties of its class, and asexual reproduction of my new variety by cuttings, grafting and budding, as performed by me at Decatur, Illinois, shows that these characteristics and distinctions come true to form and are established and transmitted through succeeding propagations.

The accompanying drawings show typical specimens of my new variety, one of said drawings showing in black-and-white a young bench plant, and the other drawing showing on a somewhat enlarged scale and in color specimens of the flowers and foliage in different stages of development, with the colors depicted as nearly true as it is reasonably possible to make the same in a color illustration of this character.

The following is a detailed description of my new variety, with color terminology in accordance with Wilson's Horticultural Colour Chart, except where general color terms of ordinary dictionary significance are obvious:

Type: Hardy; bush; greenhouse; seedling; for cut flowers and for garden decoration.
Class: Hybrid tea.
Breeding: Seedling.
*Seed parent.*—"Ophelia."
*Pollen parent.*—"Curlywhite."
Propagation: Holds its distinguish characteristics through succeeding propagations by cuttings, grafting and budding.

FLOWER (Observations made from specimens grown and observed at Decatur, Illinois.)

Continuity: Continuous.
Fragrance: Moderate; citrus.
Flowers borne: Singly; on strong, medium length stems.
Quantity of bloom: Abundant, both outdoors and in greenhouse.
Bud:
*Peduncle.*—Short; heavy; erect; stiff; smooth. Color—Pod Green, Plate o61, page 120.
*Before calyx breaks.*—Size—medium.
Form—long; pointed; with very few foliaceous appendages on the surface of the bud; with slender, stout foliaceous parts extending beyond the tip of the bud equal to ½ of its length.
Color—from Spinach Green, Plate o960, page 187 to Spinach Green, Plate o960/2, page 187.
*As calyx breaks.*—Color—from Spinach Green, Plate o960, page 187 to Spinach Green, Plate o960/1, page 187.
*As first petal opens.*—Size—large.
Form—globular.
Color—outside—Chartreuse Green, Plate 663/3, page 90; inside—Chartreuse Green, Plate 663/3, page 90.
*Opening.*—Opens up well; all flowers open slowly; no "sticking" of petals; higher than normal temperatures slightly increase opening rate.

Bloom:
*Size (when fully open).*—Large; from 3¾ to 4½ inches.
*Petalage.*—Semi-double; from 22 to 24 petals; arranged regularly.
*Form.*—Flat top, with open cupped center, becoming wider and cupped center giving way to somewhat flat-line top as outer petals unfurl; petals at first being tightly rolled inward, but becoming later at maturity loosely rolled outward.
Petals:
*Texture.*—Thick; leathery; with both inside and outside satiny.
*Shape.*—Obtuse, with blunt end downward; upper half of petals have wavy or curly edges; all petals have substantially same outline, but inside petals are smaller; color of both faces of petals is the same.

This description of a newly opened flower was made from a rose grown in a greenhouse in the month of October at Decatur, Illinois:

Color:
*Outside petal.*—Outside surface—Chartreuse Green, Plate 663/3, page 90. Inside surface—Chartreuse Green, Plate 663/3, page 90.
*Intermediate petal.*—Outside surface—Chartreuse Green, Plate 663/2, page 90. Inside surface—Chartreuse Green, Plate 663/2, page 90.
*Inner petal.*—Outside surface—Chartreuse Green, Plate 663/1, page 90. Inside surface—Chartreuse Green, Plate 663/1, page 90.

This description was made from a rose that was open for 3 days in a greenhouse in the month of October at Decatur, Illinois:

Color:
*Outside petal.*—Outside surface—pure white; comparable to Easter lily when flowers are in full bloom. Inside surface—pure white.
*Inside petal.*—Outside surface—much paler or lighter than Chartreuse Green, Plate 663/3. Inside surface—much paler or lighter than Chartreuse Green, Plate 663/3.
General color effect:
*Newly opened flower.*—Light pale Chartreuse Green.
*3-days open.*—Easter lily white.
Behavior: Petals hang on, turning brown; cold weather retards and hot weather accelerates maturity.
Flower longevity: On bush in garden—5 days in October. Cut flowers grown outdoors and kept at living-room temperatures—6 days in October. Cut flowers grown in greenhouse and kept at living-room temperatures—6 days in October.

REPRODUCTIVE ORGANS

Stamens: Medium number; arranged regularly about pistils. Color—Persimmon Orange, Plate 710/3, page 91.
Filaments: Long; most with anthers. Color—yellow.
Anthers: Large; all open at once. Color—reddish.
Pollen: Abundant. Color—gold.
Pistils: Many.
Styles: Uneven; medium length; heavy; bunched.
Stigma: Color—yellow.

Ovaries: All enclosed in calyx.
Hips: Globular; smooth; walls thick and fleshy. Color—reddish orange.
Sepals: Permanent; long; straight-pointed. Color—Spinach Green, Plate o960/1, page 187.
Seeds: Many; large.

PLANT

Foliage:
*Leaves.*—Compound of 5 leaflets; abundant; medium large; very heavy and leathery.
*Leaflets.* — Shape — oval. Base — round. Apex—acute. Margin—serrate.
*Color.*—Mature: upper surface—Spinach Green, Plate o960/1, page 187; under surface—Spinach Green, Plate o960/3, page 187. Young: upper surface—Spirea Red, Plate o25/2, page 112; under surface—China Rose, Plate o24/2, page 111.
*Rachis (the supporting stem of the compound leaf).*—Heavy.
Upper side—smooth; with wide, single groove or channel.
Under side—extremely smooth.
*Stipules.*—Moderately long; narrow; with long points turning out at an angle of 45°.
*Disease resistance.*—Resistant to mildew and blackspot, as determined by comparison with other varieties grown under comparable cultural conditions at Decatur, Illinois.

Growth:
*Habit.*—Bushy; upright.
*Growth.*—Very vigorous.

*Canes.*—Heavy.
*Main stems.*—Color—bright green.
Thorns—few; medium-long; straight; with long, narrow base.
Prickles—none.
Hairs—none.
*Branches.*—Color—bright green.
Thorns—few; medium-long; straight; with long, narrow base.
Prickles—none.
Hairs—none.
*New shoots.*—Color—bright red.
Thorns—few; medium length; straight; with long, narrow base.
Prickles—none.
Hairs—none.

I claim:

A new and distinct variety of rose plant of the hybrid tea class, substantially as herein shown and described, characterized particulary as to novelty by the distinctive white color of its flowers, by its relatively long pointed buds, by the relative hardness of the petals of its flowers and their consequent good shipping and keeping qualities, by its abundant and leathery foliage and the consequent good resistance thereof to mildew and blackspot, by the habit of its foliage in growing relatively close to the base of the flowers and the consequent absence of naked stems, and by its habit of bearing flowers on relatively heavy and stiff stems.

No references cited.